(12) United States Patent
Schroen et al.

(10) Patent No.: US 12,077,911 B2
(45) Date of Patent: Sep. 3, 2024

(54) PREDICTIVE CONTROL SYSTEM AND METHOD FOR BROWN WASHING TREATMENT IN PULP MILLS

(71) Applicant: Buckman Laboratories International, Inc., Memphis, TN (US)

(72) Inventors: Mark D. Schroen, Moseley, VA (US); Sergio Arreola, Pearland, TX (US); Robert Brian White, Collierville, TN (US); Richard Lusk, Nesbit, MS (US); Nate Brandeburg, Memphis, TN (US)

(73) Assignee: Buckman Laboratories International, Inc., Memphis, TN (US)

( * ) Notice: Subject to any disclaimer, the term of this patent is extended or adjusted under 35 U.S.C. 154(b) by 631 days.

(21) Appl. No.: 17/097,957

(22) Filed: Nov. 13, 2020

(65) Prior Publication Data

US 2021/0148047 A1    May 20, 2021

Related U.S. Application Data

(60) Provisional application No. 62/935,418, filed on Nov. 14, 2019.

(51) Int. Cl.
*D21C 3/22* (2006.01)
*D21C 3/24* (2006.01)
(Continued)

(52) U.S. Cl.
CPC ............... *D21C 3/228* (2013.01); *D21C 3/24* (2013.01); *D21C 9/02* (2013.01); *D21C 9/06* (2013.01); *G01N 33/343* (2013.01)

(58) Field of Classification Search
CPC .................................... D21C 9/06; D21C 9/02
See application file for complete search history.

(56) References Cited

U.S. PATENT DOCUMENTS 1,107,289 A     8/1914   Glauber
4,700,561 A    10/1987   Dougherty
(Continued)

FOREIGN PATENT DOCUMENTS

EP     1496154 B1    11/2006
EP     1318229 B1     4/2007
(Continued)

OTHER PUBLICATIONS

Horton et al., Practical Experience with On-Line Entrained Air Testing and Defoamer Control, 2007 TAPPI Papermakers and PIMA International Leadership Conference: Mar. 11-15, 2007, Jacksonville, Florida, USA.
(Continued)

*Primary Examiner* — Anthony Calandra
(74) *Attorney, Agent, or Firm* — Patterson Intellectual Property Law, P.C.

(57) ABSTRACT

A system and method are provided for predictive control of brown stock treatment at a pulp mill. Various online sensors generate output signals representative of actual values for respective process characteristics, each of which are directly or indirectly affected by adjustments to corresponding process variables. A controller uses the output signals or associated measurement data to dynamically set target values for the process characteristics based on a predicted impact of control responses for corresponding process variables. The controller further generates control signals to actuators associated with the respective process variables based on detected variations between the respective actual values and target values. Exemplary brown stock washing control systems may optimize various types of brown stock washing configurations, including for example vacuum drum washers, compaction baffle washers, chemiwashers, direct displacement washers and wash presses. Cloud-based analytics
(Continued)

and machine learning may also be implemented to improve the control algorithms over time.

11 Claims, 2 Drawing Sheets

(51) Int. Cl.
*D21C 9/02* (2006.01)
*D21C 9/06* (2006.01)
*G01N 33/34* (2006.01)

(56) References Cited

U.S. PATENT DOCUMENTS

| | | | |
|---|---|---|---|
| 4,732,651 A * | 3/1988 | Lisnyansky | D21C 9/02 162/49 |
| 4,840,704 A | 6/1989 | Seymour | |
| 6,074,522 A | 6/2000 | Seymour | |
| 6,450,006 B1 | 9/2002 | Dougherty | |
| 6,935,164 B2 | 8/2005 | Liljenberg et al. | |
| 7,083,049 B2 | 8/2006 | Schabel | |
| 7,715,929 B2 | 5/2010 | Skourup et al. | |
| 7,817,150 B2 | 10/2010 | Reichard et al. | |
| 8,808,499 B2 * | 8/2014 | Bylander | D21D 1/40 162/61 |
| 9,371,613 B1 | 6/2016 | Lobo et al. | |
| 9,477,936 B2 | 10/2016 | Lawson et al. | |
| 9,529,348 B2 | 12/2016 | Kephart et al. | |
| 9,675,905 B2 | 6/2017 | Mudaly | |
| 2004/0098148 A1 | 5/2004 | Retlich et al. | |
| 2004/0134630 A1 | 7/2004 | Lahtinen et al. | |
| 2004/0260421 A1 | 12/2004 | Persson et al. | |
| 2009/0319058 A1 | 12/2009 | Rovaglio et al. | |
| 2010/0256795 A1 | 10/2010 | Mclaughlin et al. | |
| 2010/0257227 A1 | 10/2010 | Mclaughlin et al. | |
| 2010/0257228 A1 | 10/2010 | Staggs et al. | |
| 2012/0251996 A1 | 10/2012 | Jung et al. | |
| 2015/0053358 A1 | 2/2015 | Ban et al. | |
| 2017/0068422 A1 | 3/2017 | Rahul U et al. | |
| 2018/0144271 A1 | 5/2018 | Schlitt et al. | |
| 2018/0187376 A1 * | 7/2018 | Mackie | B01D 19/0063 |
| 2019/0264387 A1 * | 8/2019 | Orgård | D21C 9/18 |

FOREIGN PATENT DOCUMENTS

| | | |
|---|---|---|
| EP | 2293164 A1 | 3/2011 |
| EP | 2469466 A1 | 6/2012 |
| JP | 2004504509 A | 2/2004 |
| WO | 2018125869 A1 | 7/2018 |

OTHER PUBLICATIONS

Mirza et al., "Foam and Entrained Air Management: A Practical Perspective," Chpt. 4 of Applications of Wet-End Paper Chemistry, 2nd ed., Dordrecht, Springer, 2009, pp. 53-72.

International Search and Written Opinion of corresponding patent application No. PCT/US2020/060507, dated Mar. 5, 2021, 11 pages (not prior art).

* cited by examiner

PREDICTIVE CONTROL SYSTEM AND METHOD FOR BROWN WASHING TREATMENT IN PULP MILLS

CROSS-REFERENCES TO RELATED APPLICATIONS

This application claims benefit under 35 USC. § 119(e) of U.S. Provisional Patent Application No. 62/935,418, filed Nov. 14, 2019.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

FIELD OF THE INVENTION

The present invention relates generally to control systems and methods for pulp mills. More particularly, the present invention relates to supervisory and standalone control systems and methods for brown stock washing across multiple potential configurations.

BACKGROUND

Conventional brown stock washing systems in pulp mills are designed to separate pulp from black liquor. Water is used in a counter current washing system to facilitate washing the black liquor from the pulp. Pulp mill operators face the challenge of balancing improved separation versus the cost of using water for separation. Process variability from a range of factors (including, e.g., temperature, pH, conductivity, Kappa, wood species, consistency, entrained air, fiber freeness, soap concentration, residual alkali, etc.) makes it difficult to maintain peak washing efficiency. The result is decreased efficiency, which leads to higher manufacturing cost or lost revenue from lower production rates.

The most common techniques used in the pulp and paper industry are reactive. Shower flow rates to the brown stock washing process are adjusted based on the conductivity of the filtrate on the final stage of washing. Vat dilution rates on washers are adjusted manually by operators for course control of washer speeds and/or vat levels. Defoamer and drainage aid may be controlled proportionally based on production rate, with manual adjustments made by operators in response to changes in vat levels, washer speeds and conductivity.

One inherent limitation of conventional methods is that they are reactive in nature. These techniques respond to shifts in the washing system balance, and often rely on manual operator intervention. One of skill in the art may appreciate that the changes made online by operators can actually lead to more process variation.

It would be desirable to provide holistic process control of the brown stock washing process to allow for proactive control of the brown stock washing system, substantially in real time or at any given selected time. However, the inherently dynamic nature of the brown stock washing process has traditionally made predictive analysis and associated process corrections extremely difficult and unreliable.

BRIEF SUMMARY

In accordance with various embodiments as disclosed herein, the above-referenced objective of holistic process control of the brown stock washing process is achieved by maintaining optimum efficiency of each washer, resulting in more stable control of the brown stock washing process and improved washing efficiency.

Briefly stated, systems and methods of the present disclosure reduce process variability and further optimize critical operational parameters such as washer speeds, shower flows, dilution ratios and chemical feeds (e.g., defoamers and drainage aids). An exemplary standalone control system for brown stock washing integrates sensing devices (such as, e.g., an ECHOWISE® entrained air monitor) and a controller into a single digitally supported package that can be integrated within and/or implemented alongside a pulp mill's distributed controls system (DCS). The components of this control system may include a controller, entrained air monitor(s) and other instrumentation, telemetry for remote access to the controller, and a cloud-based analytics engine that provides adaptive algorithms for controlling both brown stock washing process variables and chemical additives. The DCS may be used to collect the inputs for the control algorithms, defoamer feed skids and drainage aid feed skids.

The brown stock washing control system and method may preferably optimize multiple types of brown stock washing configurations, including but not limited to systems with vacuum drum washers, compaction baffle washers, chemi-washers, direct displacement washers, horizontal belt washers, pressure diffusers, and wash presses.

In a particular embodiment of a system as disclosed herein for predictive control of brown stock treatment at a pulp mill, multiple online sensors are configured to generate output signals representative of actual values for respective process characteristics. For example, a first online sensor generates output signals representative of actual values for a first process characteristic which is directly affected by adjustments to at least a first process variable, and a second online sensor generating output signals representative of actual values for a second process characteristic which is directly affected by adjustments to at least a second process variable. The second process variable is at least indirectly affected by adjustments to the first process variable. At least first and second actuators are configured to regulate actual values for the first and second process variables, respectively. A controller collects the output signals from the plurality of online sensors and determines measurement data corresponding to actual values for at least the first and second process characteristics. The controller dynamically sets target values for the first process characteristic and the second process characteristic, respectively, based on a predicted impact of corresponding control responses for at least the first process variable and the second process variable. The controller then generates control signals to the actuators associated with one or more of the at least first process variable and the second process variable based on detected variations between the respective actual values and target values.

In one exemplary aspect of the aforementioned embodiment, each of the respective first and second process variables have corresponding optimal ranges or threshold levels. The target values are dynamically set for the first process characteristic and the second process characteristic, respectively, further based on the optimal ranges or threshold levels and a predicted impact thereon of corresponding control responses for at least the first process variable and the second process variable.

In another exemplary aspect, a user interface is generated in association with a user computing device, and the controller provides the collected signals or measurement data corresponding to actual values for at least the first and second process characteristics for display via the user interface. The user interface may further enable user specification of one or more of the optimal ranges or threshold levels respectively corresponding to the first and second process variables.

In another exemplary aspect, the first sensor may be an entrained air sensor (e.g., an ECHOWISE® unit offered by the Applicant) that is configured to generate output signals representative of an entrained air level as the first process characteristic, and the first process variable corresponds to a defoamer flow rate.

In another exemplary aspect, the second sensor is a washer speed sensor configured to generate output signals representative of washer speed as the second process characteristic, and the second process variable corresponds to a vat dilution rate.

The second sensor may alternatively be a washer speed sensor configured to generate output signals representative of washer speed as the second process characteristic, and the second process variable corresponds to a defoamer flow rate.

The second sensor may alternatively be a washer speed sensor configured to generate output signals representative of washer speed as the second process characteristic, and the second process variable corresponds to a defoamer pump speed and vat dilution rate.

The second sensor may alternatively be a flow meter configured to generate output signals representative of dilution flow to the washer as the second process characteristic, and the second process variable corresponds to a defoamer pump speed.

In another exemplary aspect, the plurality of online sensors further comprises a third online sensor generating output signal representative of actual values for a third process characteristic which is directly affected by adjustments to at least a third process variable, and the third process variable is at least indirectly affected by adjustments to the first and second process variables. The controller further dynamically sets a target value for the third process characteristic based on a predicted impact of corresponding control responses for at least the first, second, and third process variables, and accordingly generates control signals to a third actuator based on detected variations between the actual values and target values for the third process characteristic.

In another exemplary aspect: the first sensor generates output signals representative of an entrained air level as the first process characteristic, and the first process variable corresponds to a defoamer flow rate; the second sensor generates output signals representative of washer speed as the second process characteristic, and the second process variable corresponds to a vat dilution rate; the third sensor is a liquor solids meter configured to generate output signals representative of a liquid solids level as the third process characteristic, and the third process variable corresponds to a shower flow rate.

In another exemplary aspect, wherein the system further includes a plurality of cascading filtrate tanks and a corresponding plurality of washers and shower flows, the liquor solids meter is provided in association with a first filtrate tank in the plurality of cascading filtrate tanks. The controller generates the control signals to the third actuator for a shower flow rate associated with the first washer based on detected variations between the actual values and target values for the third process characteristic.

In another exemplary aspect, a conductivity sensor is provided for measuring an actual conductivity value, wherein the actual conductivity value is affected by each of a plurality of process characteristics comprising the first, second, and third process characteristics, and a plurality of process variables comprising the first, second, and third process variables. The controller dynamically sets target values for the first, second, and third process characteristics further in view of a predicted impact of corresponding control responses with respect to an optimal conductivity value, and generates the control signals to the first, second, and third actuators further in view of the dynamically set target values.

Briefly stated, such an embodiment (further for example in accordance with one or more exemplary aspects as described above) may enable the use of a machine learning environment to create dynamic algorithms for a pulp mill operator or third-party administrator to address at least pulp cleanliness and manufacturing cost. Rather than simple control algorithms, this system may allow for implementation of multivariable algorithms that are based on the individual process.

Benefits of this comprehensive control system for brown stock washing may relate to optimization of washing efficiency, which can further result in a variety of benefits to the pulp mill operator, for example: increased pulp production; increased paper production; reduced bleaching costs; reduced paper machine chemical costs; reduced defoamer and drainage aid usage; reduced energy costs; reduced soda loss (soda make-up); and/or improved pulp quality.

BRIEF DESCRIPTION OF THE SEVERAL VIEWS OF THE DRAWINGS

Numerous objects, features and advantages of the embodiments set forth herein will be readily apparent to those skilled in the art upon reading of the following disclosure when taken in conjunction with the accompanying drawings.

DETAILED DESCRIPTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

The following detailed description of embodiments of the present disclosure refers to one or more drawings. Each drawing is provided by way of explanation of the present disclosure and is not a limitation. Those skilled in the art will understand that various modifications and variations can be made to the teachings of the present disclosure without departing from the scope of the disclosure. For instance, features illustrated or described as part of one embodiment can be used with another embodiment to yield a still further embodiment.

The present disclosure is intended to cover such modifications and variations as come within the scope of the appended claims and their equivalents. Other objects, features, and aspects of the present disclosure are disclosed in the following detailed description. One of ordinary skill in the art will understand that the present discussion is a description of exemplary embodiments only and is not intended as limiting the broader aspects of the present disclosure.

Throughout the specification and claims, the following terms take at least the meanings explicitly associated herein, unless the context dictates otherwise. The meanings identified below do not necessarily limit the terms, but merely provide illustrative examples for the terms. The meaning of "a," "an," and "the" may include plural references, and the meaning of "in" may include "in" and "on." The phrase "in one embodiment," as used herein does not necessarily refer to the same embodiment, although it may.

Figure 1:
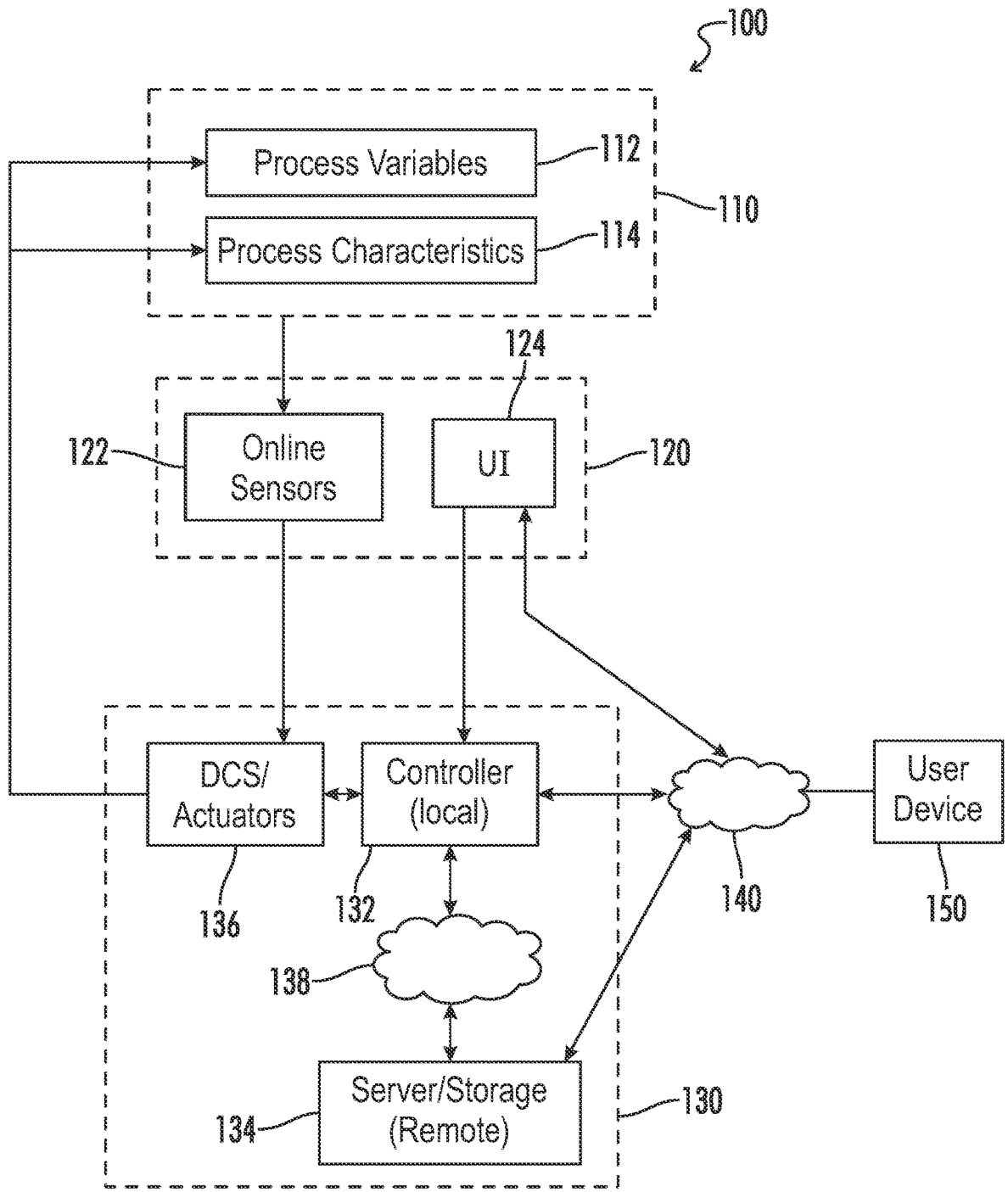
FIG. 1 is a block diagram representing an embodiment of a predictive control system as disclosed herein.

Referring first to FIG. 1, an embodiment of a predictive control system 100 as disclosed herein may be provided with respect to a brown stock treatment system and process in a pulp mill. As described in detail below, the system includes a controller that receives process information from various sensing devices and relays (e.g., entrained air meters, refractometers, coriolis mass meters, flowmeters, thermocouples, consistency transmitters, etc.). This data is used as inputs for dynamic process control algorithms to provide recommended control output for multiple process parameters in brown stock washing, which includes for example shower flows, drainage aid flow, defoamer flow, and dilution factors. Telemetry enables cloud-based analytics in real time, continuous visibility to the operators and administrators, and remote tuning of the control logic to maintain the health of the control loops, anomaly detection, and alarming. The data sent to the cloud may integrate with a machine learning environment for customization of the individual control loops and continual augmentation of those loops.

An embodiment of a production stage 110 may include various system components associated with process variables 112 and process characteristics 114. As used herein, each of the various process characteristics may be directly affected by adjustments to at least one of the process variables. For example, one of skill in the art may appreciate that an amount of entrained air (as a process characteristic) may be directly affected by adjustments to defoamer flow (as a controlled process variable).

An embodiment of a data collection stage 120 is accordingly added into the system 100 to provide real time measurements for at least the process characteristics referred to above. One or more online sensors 122 are configured to provide substantially continuous control signals representative of the process characteristics. The term "sensors" may include sensors, relays, and equivalent monitoring devices as may be provided to directly measure values for the process characteristics, or to measure appropriate derivative values from which the process characteristics may be measured or calculated. Various conventional devices are well known in the art for the purpose of continuously sensing or calculating characteristics such as entrained air, washer speed, liquor solids, conductivity, and the like, and exemplary such sensors are considered as being fully compatible with the scope of a system and method as disclosed herein. The term "online" as used herein may generally refer to the use of a device, sensor, or corresponding elements proximally located to the machine or associated process elements, and generating output signals in real time corresponding to the desired process characteristics, as distinguished from manual or automated sample collection and "offline" analysis in a laboratory or through visual observation by one or more operators.

Individual sensors may be separately implemented for the respective output signals to be collected, or in some embodiments one or more individual sensors may provide respective output signals that are implemented for the calculation of multiple variables. Individual sensors may be separately mounted and configured, or the system may provide a modular housing which includes a plurality of sensors or sensing elements. Sensors or sensor elements may be mounted permanently or portably in a particular location respective to production stage, or may be dynamically adjustable in position so as to collect data from a plurality of locations during operation.

One or more additional online sensors may provide substantially continuous measurements with respect to various controlled process variables.

A user interface 124 is further provided and configured to display process information and/or to enable operator input regarding additional parameters and/or coefficients. For example, an operator may be able to selectively monitor process characteristics and process variables in real-time, and also select control parameters such as threshold levels and/or optimal ranges for one or more of the controlled process characteristics. The term "user interface" as used herein may unless otherwise stated include any input-output module with respect to the controller and/or the hosted data server including but not limited to: a stationary operator panel with keyed data entry, touch screen, buttons, dials or the like; web portals, such as individual web pages or those collectively defining a hosted website; mobile device applications, and the like. Accordingly, one example of the user interface may be as generated remotely on a user computing device 150 and communicatively linked to the remote server 134 and/or the local controller 132.

The term "continuous" as used herein, at least with respect to the disclosed measurements, does not require an explicit degree of continuity, but rather may generally describe a series of online measurements corresponding to physical and technological capabilities of the sensors, the physical and technological capabilities of the transmission media, the physical and technological capabilities of the controller and/or interface configured to receive the sensor output signals, and/or the requirements of the associated control loop(s). For example, measurements may be taken and provided periodically and at a rate slower than the maximum possible rate based on the relevant hardware components, based on a control configuration which smooths out input values over time or otherwise does not benefit from an increased frequency of input data, and still be considered "continuous."

The online measurement data from the various sensors 122, and the input data from one or more users via the user interface, are provided to a processing and control stage 130, an embodiment of which is represented in FIG. 1 as including a controller 132. The controller 132 may be a "local" controller configured to directly receive the aforementioned signals and perform specified data processing and control functions, while separately corresponding with a remote server 134 (or cloud-based computing network) via a communications network 138. Generally speaking, the output signals may be provided from individual sensors to the DCS 136, which then passes along the output signals or derivative measurement data therefrom to the controller. In some contexts, the DCS itself may derive measurements for one or more process characteristics from other sensed values and generate representative output signals to the controller. In still other contexts, the controller may receive output signals directly from one or more online sensors and bypass the DCS. One of skill in the art may appreciate that these and other potential configurations are within the scope of the present disclosure unless otherwise specifically noted.

In an embodiment (not shown), a conversion stage may be added for the purpose of converting raw signals from one or more of the online sensors 122 to a signal compatible with the input requirements of the DCS 136 or controller 132. Alternatively, or in addition, a conversion stage (or unit) may be provided to convert raw signals from the DCS to satisfy input requirements for the controller. A conversion stage may relate not only to input requirements but also may further be provided for data security between one or more sensors and the DCS or controller as described above, and/or further between the DCS and the controller, and/or between the controller and a user computing device, for example to encrypt, decrypt, or otherwise selectively enable access to signals between respective devices.

The term "communications network" as used herein with respect to data communication between two or more system components or otherwise between communications network interfaces associated with two or more system components may refer to any one of, or a combination of any two or more of, telecommunications networks (whether wired, wireless, cellular or the like), a global network such as the Internet, local networks, network links, Internet Service Providers (ISP's), and intermediate communication interfaces. Any one or more recognized interface standards may be implemented therewith, including but not limited to Bluetooth, RF, Ethernet, and the like.

The controller 132 may be integrated within or otherwise operate cooperatively alongside an existing distributed control system 136 of the pulp mill components. For example, the controller 132 may typically generate the control signals to the various actuators via the DCS 136, or in some embodiments the controller 132 may generate control signals directly to some or all of the various actuators associated with controller process variables. In an embodiment, the controller 132 may be configured to perform each of the otherwise distinguished local and distributed functions of the DCS 136.

An exemplary and non-limiting recitation of online sensors, relays and measurements associated with the data collection stage 120 and the pulp mill DCS 136 may include flow meters, valve positions, vacuum gauges, motor load, level indicators, thermometers, pH meters, mass meters, refractometers, entrained air monitors (e.g., ECHOWISE®), tachometers, pressure gauges, and interlock signals.

The controller 132 may be designed to communicate via Modbus RTU, TCP/IP or via discrete signals to and from the DCS 136 or other process measurement, monitoring and control devices. Additionally, the controller can communicate wirelessly using a transmitter and receiver with any Modbus RTU, TCP/IP or discrete capable device.

Terms such as "controller" or "computer" as used herein may refer to, be embodied by or otherwise included within a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed and programmed to perform or cause the performance of certain acts, functions and algorithms described herein. A general-purpose processor can be a microprocessor, but in the alternative, the processor can be a microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

Depending on the embodiment, certain acts, events, or functions of any of the algorithms described herein can be performed in a different sequence, can be added, merged, or left out altogether (e.g., not all described acts or events are necessary for the practice of the algorithm) Moreover, in certain embodiments, acts or events can be performed concurrently, e.g., through multi-threaded processing, interrupt processing, or multiple processors or processor cores or on other parallel architectures, rather than sequentially.

The steps of a computer-implemented method, process, or algorithm described in connection with the embodiments disclosed herein can be embodied directly in controller hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of computer-readable medium known in the art. An exemplary computer-readable medium can be coupled to the processor such that the processor can read information from, and write information to, the memory/storage medium. In the alternative, the medium can be integral to the processor. The processor and the medium can reside in an ASIC. The ASIC can reside in a user terminal. In the alternative, the processor and the medium can reside as discrete components in a user terminal.

In an embodiment, the local controller 132 and/or the remote server 134 from the data processing and control stage 130 may be communicatively linked to a proprietary cloud-based data storage. The data storage may for example be configured to obtain, process and aggregate/store data for the purpose of developing correlations over time, improving upon existing linear regressions or other relevant iterative algorithms, etc. The controller 132 may be configured to include certain correlations, equations and/or algorithms in a local data storage, while continuously or periodically transmitting relevant data to the remote server, and for example periodically retrieving any changes to the correlations, equations and/or algorithms as may be determined with the additional input data over time via, e.g., machine learning.

In certain embodiments, the remote data capability of the system may enable the application of machine learning concepts to the brown stock washing system to enhance the controls over time. One of skill in the art of brown stock washing may appreciate or otherwise be able to determine the value of many other variables in the control algorithms. The following is a non-exhaustive list of inputs that may be included in modeling of the systems: mat thickness measurement (using a tool to measure the thickness as opposed to assuming the thickness from input calculations); mat consistency measurement (using, e.g., a near-infrared light or equivalent device to measure the consistency of the mat in real time); stock temperature; filtrate temperature; shower temperature; pH of stock and filtrate; residual alkali in stock exiting the digester; conductivity in the washer vats and/or filtrate; filtrate tank levels; dropleg vacuum; Kappa measurement of the stock; fiber species; refiner loading; stock consistency; vacuum box levels on horizontal belt washers; vacuum on horizontal belt washers; headbox pressure on direct displacement and compaction baffle washers; washer drum motor loads; repulper motor loads; and/or stock pump motor loads.

Figure 2:
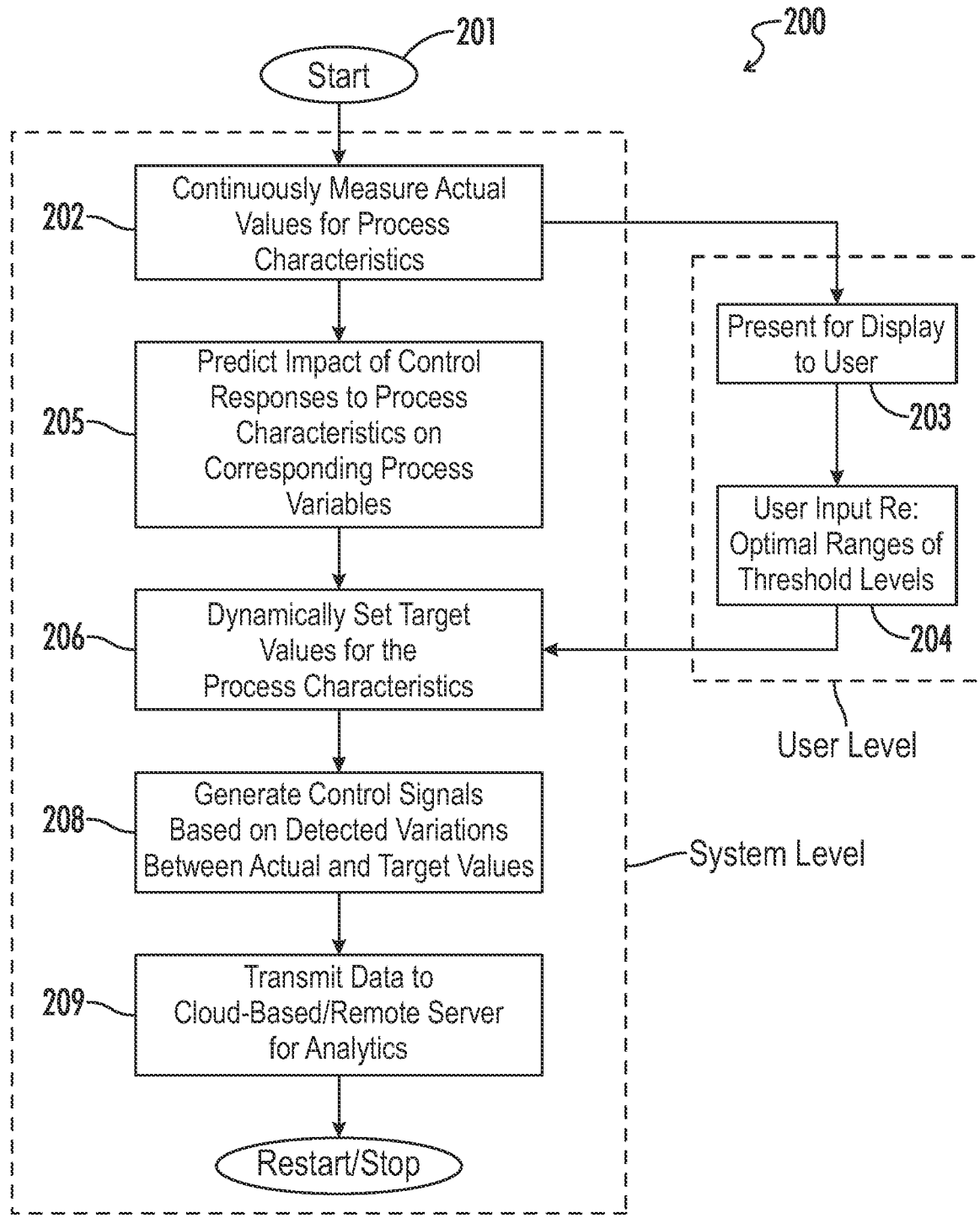
FIG. 2 is a flowchart representing an embodiment of a predictive control method as disclosed herein.

Referring now to FIG. 2, an embodiment may now be described for an exemplary method 200 for predictive control of brown stock treatment in real time, substantially in accordance with an embodiment of the system 100 as disclosed above.

In the particular embodiment, upon starting the process (step 201) the online sensors 122 continuously generate output signals corresponding to actual values respective process characteristics 114 (step 202). The output signals may be provided in raw form for conversion, calibration, and otherwise for measurement of the actual values of the process characteristics, or the measurements may be directly output from the sensors to the local controller 132.

The following steps may be performed by either of the local controller or the remote server. In a particularly exemplary embodiment, the local controller performs all of the data processing and control operations as required for ordinary functioning of the process, but may pass information along to a remote server for cloud-based analytics and data processing. In an embodiment, the controller may be configured to access the remote server, or provide access to the remote server, for system updates such as for example to update the software or algorithm programming, configurations and the like. However, the scope of a process as disclosed herein is not structurally limited to this configuration unless otherwise specifically noted.

In step 203 of the present embodiment, the controller 132 presents the measured actual values (or alternatively said values are provided directly from the corresponding online sensors 122) to a user interface 124 for display and monitoring purposes. Various exemplary screens of the user interface may be designed to identify functions such as operation, configuration, analytics and system alarms. The controller may also provide a layer of security by password protecting these functions or providing limited accessibility to users based on user classification. In step 204, the user interface may enable user input regarding optimal ranges or threshold levels for one or more controllable process variables.

In step 205 of the present embodiment, the controller 132 predicts an impact of subsequent control responses to process characteristics on corresponding process variables. In other words, the controller considers not only how a process characteristic itself may be optimized through control responses, but also how these control responses would impact certain process characteristics. Controller-based algorithms effectively model these interactions and correlations to optimize performance for each of the process variables and the impacted process characteristics, thereby minimizing the potential for variability and negative feedback loops.

Based on the predictions in the previous step, the controller continues in step 206 by dynamically setting target values for the process characteristics. These target values can then be implemented directly or otherwise delivered to the mill's DCS or equivalent for local implementation. For example, in step 208 the controller may generate control signals to the DCS and/or to any one or more system actuators for regulating respective process characteristics based on detected variations between the measured actual values and the dynamically set target values.

In an embodiment, the controller may in step 209 further continuously or periodically deliver data (in raw form or for example as aggregated over time) to the remote server for analytics.

The aforementioned embodiment of a system 100 and method 200 may further be described by illustrative reference to a vacuum drum washer configuration, as is generally known in the art. It should be noted that inventive aspects of the system and method may be applied for a number of alternative brown stock washer implementations, and the vacuum drum washer is only referenced for illustrative purposes.

Conventionally speaking, in such configurations dirty pulp travels through the process from beginning to end and becomes cleaner, as dirty liquor is separated from the pulp using clean water which is provided at the "clean" end and moves backwards to the "dirty" end of the process.

The water is applied to a vacuum drum washer via washing showers. A slurry of pulp and dilution water enters an inlet box and overflows into a vat with a perforated drum rotating therein. Water drains through a screen on the drum (i.e., vacuum formation zone), falling down a dropleg and creating a vacuum. This vacuum helps pull more stock and liquor onto the drum. The liquor drains through to the dropleg, but the stock (pulp) stays on the drum surface. As the drum turns, the pulp mat that is formed on the drum comes out of the vat (i.e., extraction zone) and then is hit by the washing showers that put cleaner water onto the mat (i.e., displacement zone). The dirty liquor is therefore displaced in the mat with cleaner water from the showers. This liquor also pulls through the drum down the dropleg. A take-off doctor is applied to doctor off the mat (cleaned pulp) which goes to a repulper to pass onto the next stage of washing. The clean washer surface now submerges under the vat level and the process repeats.

Defoamer is typically added with the pulp before the washer or into the cleaning showers. The defoamer helps remove air, which allows the liquor to drain through the mat of fibers more easily. Air bubbles in the mat of fiber blocks the passage of liquor and impedes drainage.

Conventional defoamer control typically involves manual setting of the flow, for example by adjustment of a pump speed, or automatic adjustments based on operator-selected changes in the production rate. However, such techniques are inherently reactive, in that the operator can only respond to observed changes in the process, and even then only by making imprecise adjustments. One problem with such reactive control is that over-usage of defoamer drives up cost and can lead to silicone carryover issues (quality issue) in the final pulp. In addition, whereas defoamer can remove the negative impact on drainage from entrained air, it does not fundamentally address other variables which impact drainage including temperature, consistency, conductivity, alkali content, fiber freeness, soap, and the like.

Embodiments of a predictive control system and method as disclosed herein may be applied in this exemplary configuration to introduce a more holistic approach to this problem, as one of many controllable process characteristics and process variables having associated impacts and correlations. An entrained air monitor (e.g., an ECHOWISE® unit as previously noted) may be used to provide continuous and real-time signals representing the entrained air, wherein the control system may receive inputs for the production rate and the entrained air value and further determine an amount of defoamer to add to the system, for example by regulating the pump speed.

The control may be applied as feedback or feed forward control, depending on the location of the entrained air sensor and the defoamer addition point. If the defoamer is added before a point where air can be released and the sensor is after that point, feedback control may be implemented wherein the system dynamically provides a setpoint for entrained air and then defoamer is adjusted to maintain that setpoint. If the sensor is located between the defoamer addition point and before the air can be released, a feed forward control is implemented because there is nowhere for the air to go before the sensor reads the air. In this case, the system may predict an amount of defoamer to add based on the amount of entrained air and the production rate in the system. Over time initial assumptions may be adjusted by the system to provide the best possible control of defoamer based on these two predictors (production rate changes and entrained air level).

One benefit of this technique is that the system adds the amount of defoamer needed to control the primary variable that the defoamer is capable of controlling, i.e., how much entrained air is in the system. This is proactive, in that defoamer is increased before increases in entrained air cause the vat levels to rise or the washer to speed up, and that the defoamer is conversely decreased when it is no longer needed. This may preferably optimize the amount of defoamer for any target level of entrained air and further take variability in entrained air out of the process. The reduction in process variability allows the entire system to run more fluidly, in that other loops can be tuned better and the system can find and eliminate other sources of variability. In other words, the washer speed now varies based on other items like consistency swings, conductivity changes, etc.

If this technique were implemented only to maintain the typical levels of entrained air, defoamer usage could be decreased substantially. However, by proactively reducing the entrained air level, the system may be able to run about the same amount of defoamer and use the additional drainage to optimize the process, providing significant value for the pulp mill operator. For example, by being proactive the system can maintain the vat level and the washer speed at more consistent settings, which allows the process to be optimized rather than constantly chasing the impact of entrained air. This may results in savings in a variety of areas including for example one or more of: increased productivity, cleaner pulp, lower bleaching costs in bleached mills, lower chemical costs in unbleached mills, lower energy costs, using less water to wash the pulp (which has to be evaporated at a cost), and reduced defoamer usage.

Accordingly, a predictive system in an exemplary embodiment as disclosed herein measures entrained air as a first process characteristic which is directly affected by changes in defoamer flow as a first process variable, and further predicts what will correspondingly happen to vat levels and washer speeds and adjusts defoamer before those variables respond—preventing them from changing.

Washer speeds are conventionally regulated automatically or manually by an operator to control vat levels and thereby prevent overflow. Using the automatic control example, as the vat level rises the washer speeds up, and as the vat level decreases the washer speed slows down. A setpoint may be entered for the vat level and a simple PID control is implemented for the washer speed.

When the washer runs "too fast" the operator knows that at any moment the vat could overflow, and when the washer is running "slow" the washer speed has plenty of ability to respond to a sudden rise in vat level. Vat level may rise because of, e.g., a production rate change or because of a lack of drainage. Therefore, an operator may typically prefer to keep the washer running slow, allowing plenty of room for error before the vat overflows.

There are numerous techniques for keeping the washer running slowly, including: increasing defoamer, decreasing the vat dilution valve position, cutting back shower flows on the washer, and/or slowing down the production rate. However, these techniques are solely focused on controlling the vat to make sure it does not overflow, and fail to properly consider an optimal washing efficiency for that washer, and resultingly the system as a whole. For example, vat dilution improves washing efficiency without using more water that needs to be evaporated, and cutting back on vat dilution reduces the washing efficiency of the washer. After defoamer has been increased to slow down the washer, it should preferably be decreased again once the vat level goes back down, but operators often choose to leave the defoamer rate up out of caution. Cutting back shower flows ultimately results in reduced pulp cleanliness. Cutting back the production rate obviously reduces the output of the system.

In an embodiment, entrained air may further be implemented as part of this control scheme. As entrained air rises, the vat level will increase, upon which the washer speed will increase, the vat dilution will decrease, and then the defoamer will increase. The control algorithms are configured to predict these events and get ahead of them, by observing the change in entrained air to proactively move the defoamer, speeding up the response of the entire control scheme and ultimately providing better controlled washer speed and washing efficiency.

Another exemplary control scheme may now be described according to a predictive control system and method as disclosed herein, involving weak black liquor solids and shower flow control.

In one conventional example an operator may measure the conductivity in washed pulp coming off a last stage washer, and decide to increase or decrease the flow setpoint of the shower water. In another conventional example, the controlled method differs in that there is an on-line conductivity probe on the filtrate dropping down to the last stage filtrate tank, and there is a conductivity setpoint that controls the shower flow.

The major challenge here, regardless of what method the mill uses, is the balance between the final conductivity (cleanliness of the pulp slurry) versus the weak black liquor solids (how much water) going to the recovery area. More water means cleaner pulp, but more water to evaporate in recovery. Less water means less water to evaporate, but leads to dirtier pulp.

There are numerous disadvantages to these conventional methods, the first of which is the undesirable lag time in control response. The filtrate tanks under the washers are large, and as the pulp changes coming into the system out of the blow tank it may take hours for the filtrate tanks to reach equilibrium. Therefore, for applications including conductivity measurement at the final stage, there is a large volume of filtrate that needs to be turned over to move the process. Regardless of which conventional control scheme described above is used, they are often adding variability by chasing swings in the process.

Another disadvantage involves soap solubility. There are multiple factors here that impact the solubility curve, the largest of which include solids (concentration), temperature, and residual alkali. Once soap separates, it cannot go back into solution. The soap entrains air in bubbles that impede drainage, and these bubbles cannot be impacted by defoamer. Therefore, soap separation typically leads to poor drainage and high defoamer usage because the operators unsuccessfully add defoamer to try to fix the drainage, with the end result being dirty pulp and/or low weak black liquor solids.

By controlling to conductivity at the end of the process, mills are susceptible to soap separation on the early stages of washing because the solids level will fluctuate wildly based on shower flow changes made for the last stage and incoming variability in the pulp. Conductivity control has no means of managing soap separation. The safest option is accordingly to run solids low, minimizing how often they cross the solubility line.

Still another disadvantage arises in that when reacting to the conductivity at the end of the process, part of the change in the final measurement in conductivity is based on dilution. When the operator adds more shower water to clean the pulp, the conductivity lowers immediately, not so much because of better washing, but because they have diluted the solids content at that measurement point. This gives a false sense of "controlling" the conductivity, when in face the sample is diluted. Ultimately this leads to a false belief that conductivity is controlled, whereas in reality the amount of material carrying forward in the process is still variable.

According to an embodiment of the predictive control system as disclosed herein, liquor solids off of the first stage filtrate tank are measured as a third process characteristic, and shower flows at the corresponding first stage washer as a third process variable are controllably adjusted. The aforementioned liquor solids measurements may for example be provided via a solids meter (e.g., Coriolis mass flowmeter, refractometer or the like) on the first stage filtrate.

In an exemplary embodiment as disclosed herein, the system obtains comprehensive data points from throughout the process to model washing efficiency. In other words, the controller can receive inputs from (or corresponding to) the entrained air sensors, washer speeds, defoamer usage, conductivity, mass meter, production rate, vat dilution flows, filtrate tank levels, residual alkali, and/or temperature, and perform predictive modeling of the final conductivity versus the incoming parameters to the first stage washer.

Implementing this predictive modeling, the weak black liquor solids target can be continuously adjusted to further maintain control of the conductivity.

As one example, a solids target of 15.5% may initially be provided for a given mill, to prevent crossing of the soap line. This number may be adjusted seasonally (for example due to temperature changes from winter to summer) but generally run as high as possible, without allowing cross over of the soap solubility limit.

In a predictive system as disclosed herein, additional data in the mill may be used to continually predict a soap solubility limit. This enables the system to maintain a proper solids level based on changes in temperature and residual alkali coming into the washers. It is unnecessary in this case to manually change the setpoint several times per year, as it is now automatically adjusted based on temperature changes. This may prevent the odd excursion in conventional applications, typically because of a temperature swing or changes to the digester cooking process (residual alkali).

Furthermore, all of the aforementioned variables may be used to force the solids target lower when needed to help maintain conductivity in tighter control. For mills that are more focused on the impact of the variability of conductivity on their process (final pulp cleanliness) than maintaining the liquor solids to recovery, the system can adapt to changes in washing efficiency in the system to dynamically lower the solids setpoint and better maintain the conductivity at the far end. Even assuming arguendo an upper limit on the solids based for example on soap solubility, the system can adjust the solids setpoint to maintain the best final conductivity possible.

Briefly stated, substantially optimal shower flow/solids control may be provided by a system and method as disclosed herein, dependent upon the individual stages running at a consistent efficiency. In an exemplary and non-limiting embodiment, all three of the aforementioned schemes may work in concert, wherein the consistent performance in the individual washers allows for a better correlation of how a change in solids will impact the final conductivity on the washer line. In other words, the solids control can behave much better in concert with the other controls. By tuning each loop, and particularly in view of the measurement and control of entrained air, effective modeling and prediction of the process becomes possible, as compared to what is possible in conventional mills due to excessive variability.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The previous detailed description has been provided for the purposes of illustration and description. Thus, although there have been described particular embodiments of a new and useful invention, it is not intended that such references be construed as limitations upon the scope of this invention except as set forth in the following claims.

What is claimed is:

1. A computer-implemented method for predictive control of brown stock treatment at a pulp mill, the method comprising:
   continuously measuring, via a plurality of online sensors, actual values for respective process characteristics comprising an entrained air level, a vat level, and a washer speed, wherein the entrained air level is directly affected by adjustments to at least a defoamer flow rate, and the vat level is directly affected by adjustments to at least a vat dilution rate;
   dynamically setting target values for the entrained air level and the vat level, respectively, based on a predicted impact of corresponding control responses for at least the defoamer flow rate and the vat dilution rate; and
   generating control signals for actuators associated with defoamer flow rate and the vat dilution rate based on detected variations between the respective actual values and target values for the entrained air level and vat level; and
   generating control signals to the actuator associated with washer speed based on detected variations between the actual and target values for the vat level.

2. The computer-implemented method of claim 1, wherein:
   each of the defoamer flow rate and the vat dilution rate have corresponding optimal ranges or threshold levels, and
   the target values are dynamically set for the entrained air level and the vat level, respectively, further based on the optimal ranges or threshold levels and a predicted impact thereon of corresponding control responses for at least the defoamer flow rate and the vat dilution rate.

3. The computer-implemented method of claim 1, further comprising providing the collected signals or measurement data corresponding to actual values for at least the entrained air level and the vat level for display via a user interface.

4. The computer-implemented method of claim 3, further comprising enabling user specification, via the user interface and a communications network linked thereto, of one or more of the optimal ranges or threshold levels respectively corresponding to the defoamer flow rate and the vat dilution rate.

5. The computer-implemented method of claim 1, wherein the plurality of online sensors further comprises a liquid solids meter configured to generate output signals representative of actual values for a liquid solids level which is directly affected by adjustments to at least a shower flow rate, wherein the shower flow rate is at least indirectly affected by adjustments to defoamer flow rate and the vat dilution rate, the method further comprising:
  dynamically setting a target value for the liquid solids level based on a predicted impact of corresponding control responses for at least the defoamer rate, the vat dilution rate, and the shower flow rate, and
  generating control signals to an actuator associated with the shower flow rate based on detected variations between the actual values and target values for the liquid solids level.

6. The computer-implemented method of claim 5, wherein the pulp mill further comprises a plurality of cascading filtrate tanks and a corresponding plurality of washers and shower flows, and the liquor solids meter is provided in association with a first filtrate tank in the plurality of cascading filtrate tanks, wherein the method further comprises:
  generating the control signals to the third actuator for a shower flow rate associated with the first washer based on detected variations between the actual values and target values for the liquid solids level.

7. The computer-implemented method of claim 6, wherein the pulp mill further comprises a conductivity sensor for measuring an actual conductivity value, and wherein the actual conductivity value is affected by each of a plurality of process characteristics comprising the first, second, and third process characteristics, and a plurality of process variables comprising the defoamer rate, the vat dilution rate, and the shower flow rate, the method further comprising:
  dynamically setting target values for the entrained air level, the washer speed, and the liquid solids level further in view of a predicted impact of corresponding control responses with respect to an optimal conductivity value, and
  generating the control signals to the respective actuators further in view of the dynamically set target values.

8. A system for predictive control of brown stock treatment at a pulp mill, the system comprising:
  a plurality of online sensors configured to generate output signals representative of actual values for respective process characteristics comprising an entrained air level, a vat level, and a washer speed;
  wherein the entrained air level is directly affected by adjustments to at least a defoamer flow rate, and the vat level is directly affected by adjustments to at least a vat dilution rate;
  a plurality of actuators configured to regulate actual values for the defoamer flow rate, the vat dilution rate, and the washer speed, respectively;
  a controller configured to
    dynamically set target values for the entrained air level and the vat level, respectively, based on a predicted impact of corresponding control responses for at least the defoamer flow rate and the vat dilution rate;
    generate control signals to the actuators associated with defoamer flow rate and the vat dilution rate based on detected variations between the respective actual values and target values for the entrained air level and vat level; and
    generate control signals to the actuator associated with washer speed based on detected variations between the actual and target values for the vat level.

9. The system of claim 8, wherein:
the plurality of online sensors comprises a liquid solids meter configured to generate output signals representative of a liquid solids level which is directly affected by adjustments to a shower flow rate;
wherein the shower flow rate is at least indirectly affected by adjustments to defoamer flow rate and the vat dilution rate; and
the controller is further configured to
  dynamically set a target value for the liquid solids level based on a predicted impact of corresponding control responses for at least the defoamer rate, the vat dilution rate, and the shower flow rate, and
  generate control signals to an actuator associated with the shower flow rate based on detected variations between the actual values and target values for the liquid solids level.

10. The system of claim 9, further comprising:
a plurality of cascading filtrate tanks and a corresponding plurality of washers and shower flows,
wherein the liquor solids meter is provided in association with a first filtrate tank in the plurality of cascading filtrate tanks, and
wherein the controller is configured to generate the control signals to the actuator for a shower flow rate associated with the first washer based on detected variations between the actual values and target values for the liquid solids level.

11. The system of claim 10, further comprising:
a conductivity sensor for measuring an actual conductivity value;
wherein the actual conductivity value is affected by each of a plurality of process characteristics comprising the entrained air level, the washer speed, and the liquid solids level, and a plurality of process variables comprising the defoamer flow rate, the vat dilution rate, and the shower flow rate;
the controller is configured to:
  dynamically set target values for the entrained air level, the washer speed, and the liquid solids level further in view of a predicted impact of corresponding control responses with respect to an optimal conductivity value, and
  generate the control signals to the respective actuators further in view of the dynamically set target values.

* * * * *